(12) United States Patent
Tsuzuki et al.

(10) Patent No.: US 8,453,492 B2
(45) Date of Patent: Jun. 4, 2013

(54) BREATH ALCOHOL MEASURING APPARATUS

(75) Inventors: Hanzo Tsuzuki, Fuji (JP); Kentaro Sato, Fuji (JP); Yuji Yamazawa, Fuji (JP)

(73) Assignee: Tokai Denshi, Inc., Fuji-shi, Shizuoka (JP)

( * ) Notice: Subject to any disclaimer, the term of this patent is extended or adjusted under 35 U.S.C. 154(b) by 179 days.

(21) Appl. No.: 13/162,030

(22) Filed: Jun. 16, 2011

(65) Prior Publication Data

US 2011/0308297 A1 Dec. 22, 2011

(30) Foreign Application Priority Data

Jun. 17, 2010 (JP) ................. 2010-138018

(51) Int. Cl.
*G01N 33/497* (2006.01)
(52) U.S. Cl.
USPC .......................................... 73/23.3
(58) Field of Classification Search
USPC .......................................... 73/23.3
See application file for complete search history.

(56) References Cited

U.S. PATENT DOCUMENTS

| | | | | |
|---|---|---|---|---|
| 4,093,945 A | * | 6/1978 | Collier et al. | 180/272 |
| 5,020,628 A | * | 6/1991 | Bigliardi et al. | 180/272 |

FOREIGN PATENT DOCUMENTS

| | | |
|---|---|---|
| JP | 2008-170156 A | 7/2008 |
| JP | 2008-232710 A | 10/2008 |
| JP | 2009-008499 A | 1/2009 |
| JP | 4323564 B | 9/2009 |
| JP | 2010-025716 A | 2/2010 |

OTHER PUBLICATIONS

Notification of Reasons for Refusal dated Aug. 31, 2010, corresponds to Japanese Patent Application No. 2010-138018.

* cited by examiner

*Primary Examiner* — Hezron E Williams
*Assistant Examiner* — Paul West
(74) *Attorney, Agent, or Firm* — Westerman, Hattori, Daniels & Adrian, LLP

(57) ABSTRACT

When a pressure of a breath is kept to fall within a valid range, a CPU of a breath alcohol measuring apparatus updates a breath amount accumulation value that is an accumulation value of the amount of the breath blown into a mouth piece; when the breath pressure reaches the range outside the valid range, the CPU resets the breath amount accumulation value; and when the breath amount accumulation value reaches a valid breath amount, the CPU measures the alcohol concentration by an alcohol sensor. A breath pressure display portion is arranged at the position that can visually be recognized by a to-be-measured person who is blowing into the mouth piece.

22 Claims, 9 Drawing Sheets

FIG.6

| | LIGHT-EMITTING MEMBER | | | | |
|---|---|---|---|---|---|
| | 25e | 25d | 25c | 25b | 25a |
| RANGE 7 | ◐ | ○ | ○ | ○ | ○ |
| RANGE 6 | ◐ | ○ | ○ | ○ | ○ |
| RANGE 5 | ○ | ◐ | ○ | ○ | ○ |
| RANGE 4 | ○ | ○ | ● | ○ | ○ |
| RANGE 3 | ○ | ○ | ○ | ◐ | ○ |
| RANGE 2 | ○ | ○ | ○ | ○ | ◐ |
| RANGE 1 | ○ | ○ | ○ | ○ | ○ |

VALID RANGE (spans RANGE 2 to RANGE 6)

BREATH ALCOHOL MEASURING APPARATUS

BACKGROUND OF THE INVENTION

1. Field of the Invention

The present invention relates to a breath alcohol measuring apparatus that can measure a breath alcohol concentration of a to-be-measured person.

2. Description of the Related Art

There has been known a conventional breath alcohol measuring apparatus including a casing that is held by a hand of a to-be-measured person during the measurement; a mouth piece that is provided to the casing and into which a breath of the to-be-measured person is blown; an alcohol sensor that measures an alcohol concentration in the breath blown into the mouth piece; a wind sensor that measures a force of wind, which is the force of the breath blown into the mouth piece; and an OK lamp provided to the casing and indicating that the measurement of the breath alcohol concentration of the to-be-measured person is normally completed (see, for example, Patent Document 1). When a significant rise in the force of wind measured by the wind sensor is recognized, the alcohol sensor measures the alcohol concentration at the timing when the significant rise in the force of wind measured by the wind sensor is recognized, whereby the OK lamp is lighted. When an abnormal situation such as the case in which the significant rise in the force of wind measured by the wind sensor is not recognized is detected, the OK lamp is flickered so as to indicate that the to-be-measured person has to undergo the measurement again.

Patent Document 1: Jpn. Pat. Appln. KOKAI Publication No. 2008-232710

SUMMARY OF THE INVENTION

However, in the breath alcohol measuring apparatus described in Patent Document 1, the OK lamp is arranged at the position where the to-be-measured person, who is blowing into the mouth piece, cannot visually recognize the OK lamp. Therefore, the to-be-measured person, who is blowing into the mouth piece, cannot recognize whether or not he/she is blowing with the breath force within the range of the breath force that makes the measurement of the alcohol concentration by the alcohol sensor valid.

Therefore, it is difficult for the to-be-measured person to keep the breath force within the range that makes the measurement of the alcohol concentration by the alcohol sensor valid. As a result, the to-be-measured person cannot be successfully measured on the first attempt, and has to undergo the measurement again and again. For example, in the case of a breath alcohol measuring apparatus that a to-be-measured person is not used to, such as a breath alcohol measuring apparatus for a drunk driving check by a police, it is more difficult for the to-be-measured person to keep the breath force within the range that makes the measurement of the alcohol concentration by the alcohol sensor valid.

In view of this, the present invention provides a breath alcohol measuring apparatus that can allow a to-be-measured person, who is blowing, to recognize the breath force.

A breath alcohol measuring apparatus according to the present invention includes: a casing that is held by a hand of a to-be-measured person during a measurement; a breath blowing portion that is provided to the casing and into which a breath of the to-be-measured person is blown; an alcohol sensor that measures an alcohol concentration of the breath blown into the breath blowing portion; a breath force sensor that measures a force of the breath blown into the breath blowing portion; and a breath force display portion that is provided to the casing for displaying the force measured by the breath force sensor, wherein the breath force display portion is arranged at the position that can be visually recognized by the to-be-measured person who is blowing into the breath blowing portion.

With this configuration, in the breath alcohol measuring apparatus according to the present invention, the breath force display portion is arranged at the position that can be visually recognized by the to-be-measured person who is blowing into the breath blowing portion. Accordingly, the breath alcohol measuring apparatus can allow the to-be-measured person, who is blowing, to recognize the breath force.

The breath force display portion in the breath alcohol measuring apparatus according to the present invention may indicate the valid range, which is the range of the force that makes the measurement of the alcohol concentration by the alcohol sensor valid, with plural levels.

With this configuration, the breath alcohol measuring apparatus according to the present invention can allow the to-be-measured person to recognize at which level in the valid range the breath force is placed. Therefore, compared to the configuration in which only whether the breath force falls within the valid range or not is displayed, i.e., the configuration in which the valid range is displayed with one level, the breath alcohol measuring apparatus according to the present invention can allow the to-be-measured person to easily keep the breath force within the valid range.

The breath forth display portion in the breath alcohol measuring apparatus according to the present invention may include plural light-emitting members that display the force with plural levels.

With this configuration, the breath alcohol measuring apparatus according to the present invention can allow the to-be-measured person to easily recognize whether the breath force is appropriate or not, compared to the configuration in which the breath force display portion displays the breath force with a numerical value.

The plural light-emitting members in the breath alcohol measuring apparatus according to the present invention may be arranged side by side in the order of the corresponding level of the force.

With this configuration, the breath alcohol measuring apparatus according to the present invention can allow the to-be-measured person to easily recognize whether the breath force is appropriate or not, compared to the configuration in which the plural light-emitting members are arranged regardless of the order of the level of the breath force.

The light-emitting member corresponding to the middle level within the valid range in the breath alcohol measuring apparatus according to the present invention may emit light in a form different from those of the other light-emitting members.

With this configuration, the breath alcohol measuring apparatus according to the present invention can allow the to-be-measured person to easily recognize the middle level within the valid range. Therefore, the breath alcohol measuring apparatus allows the to-be-measured person to adjust the breath force such that the middle level within the valid range is displayed, whereby the to-be-measured person can easily keep the breath force within the valid range.

The breath force display portion in the breath alcohol measuring apparatus according to the present invention may indicate at least one level, which is adjacent to a level outside the valid range, of the plural levels within the valid range, and the level outside the valid range adjacent to this level, with the same display.

With this configuration, even when the breath force changes, when it is within the valid range, so that the display is the same as the display for the level outside the valid range, the breath force is still within the valid range immediately after the breath force display portion makes this display. Accordingly, the to-be-measured person adjusts the breath force in order that this display is not made, whereby the to-be-measured person can easily keep the breath force within the valid range. In the breath alcohol measuring apparatus according to the present invention, at least one level within the valid range is indicated by the display being the same as the display for the level outside the valid range. Therefore, the number of the light-emitting members can be reduced, compared to the configuration in which this level is indicated by the display different from the display for the level outside the valid range.

The breath force display portion of the breath alcohol measuring apparatus according to the present invention may include a single light-emitting member that indicates the force with the plural levels by changing a light-emitting form.

With this configuration, the breath alcohol measuring apparatus according to the present invention can reduce the arrangement space of the light-emitting member, compared to the configuration in which the breath force is displayed by the plural light-emitting members.

The breath force display portion of the breath alcohol measuring apparatus according to the present invention may be arranged at the position on a projecting portion of the casing, and at the position opposite to eyes of the to-be-measured person who is blowing into the breath blowing portion.

With this configuration, the breath alcohol measuring apparatus according to the present invention can allow the to-be-measured person, who is blowing, to easily recognize the breath force display portion visually.

EFFECT OF THE INVENTION

The breath alcohol measuring apparatus according to the present invention can allow the to-be-measured person, who is blowing, to recognize the breath force.

BRIEF DESCRIPTION OF THE DRAWINGS

FIG. 6 is a view illustrating a display example, different from the display example illustrated in FIG. 4, of the breath pressure display portion in the breath alcohol measuring apparatus illustrated in FIG. 1;

DESCRIPTION OF THE PREFERRED EMBODIMENTS

The embodiments of the present invention will be described below with reference to the drawings.

First Embodiment

A configuration of a breath alcohol measuring apparatus according to the first embodiment of the present invention will firstly be described.

Figure 1:
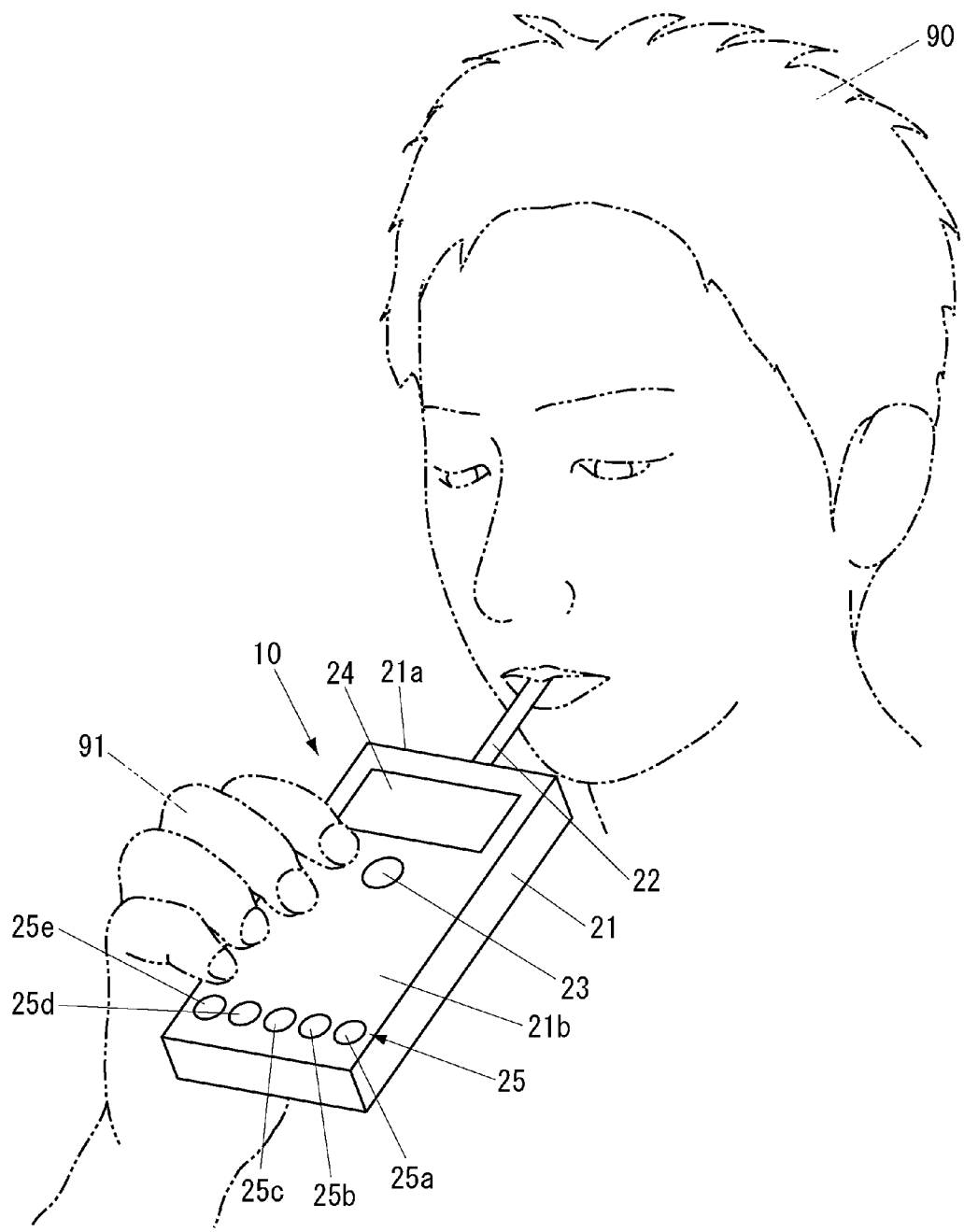
FIG. 1 is a perspective view illustrating an appearance of a breath alcohol measuring apparatus according to a first embodiment of the present invention.

FIG. 1 is a perspective view illustrating an appearance of a breath alcohol measuring apparatus 10 according to the present embodiment.

As illustrated in FIG. 1, the breath alcohol measuring apparatus 10 includes a casing 21 that is held by a hand 91 of a to-be-measured person 90 during a measurement; a mouth piece 22, serving as a breath blowing portion in the present invention, that is provided to the casing 21, that is held by the to-be-measured person 90 with his/her mouth, and into which a breath is blown; a switch 23 that is provided for starting the measurement of an alcohol concentration in the breath blown into the mouth piece 22; an alcohol concentration display portion 24 that displays the alcohol concentration in the breath blown into the mouth piece 22; and a breath pressure display portion 25, serving as a breath force display portion in the present invention, that displays the breath pressure, which is a pressure of the breath, as a force of the breath blown into the mouth piece 22.

The casing 21 is substantially a rectangular parallelepiped shape having a surface 21a on which an unillustrated breath injecting port to which the mouth piece 22 is inserted is formed, and a surface 21b that is adjacent to the surface 21a and on which the switch 23 is provided, the alcohol concentration display portion 24, and the breath pressure display portion 25.

The mouth piece 22 is provided so as to be detachable to the breath injecting port of the casing 21, so that it can be exchanged for each to-be-measured person 90.

The switch 23 is provided at the substantially center of the surface 21b of the casing 21.

The alcohol concentration display portion 24 is a display device such as an LCD (Liquid Crystal Display). The alcohol concentration display portion 24 is provided near the mouth piece 22 with respect to the switch 23 on the surface 21b of the casing 21.

The breath pressure display portion 25 includes five light-emitting members 25a to 25e. The light-emitting members 25a to 25e are light-emitting devices such as LED (Light Emitting Diode). The breath pressure display portion 25 is provided at the side opposite to the mouth piece 22 with respect to the switch 23 on the surface 21b of the casing 21, and at the position that can be visually recognized by the to-be-measured person 90 who is blowing into the mouth piece 22. The light-emitting members 25a to 25e are arranged laterally from the left to the right as viewed from the to-be-measured person 90 who is blowing into the mouth piece 22. The light-emitting member 25a and the light-emitting member 25e emit light of the same color. The light-emitting members 25b and 25d emit light of the same color that is different from the emitted color of the light-emitting members 25a and 25e. The light-emitting member 25c emits light that is different from the emitted colors of the light-emitting members 25a, 25b, 25d, and 25e.

Figure 2:
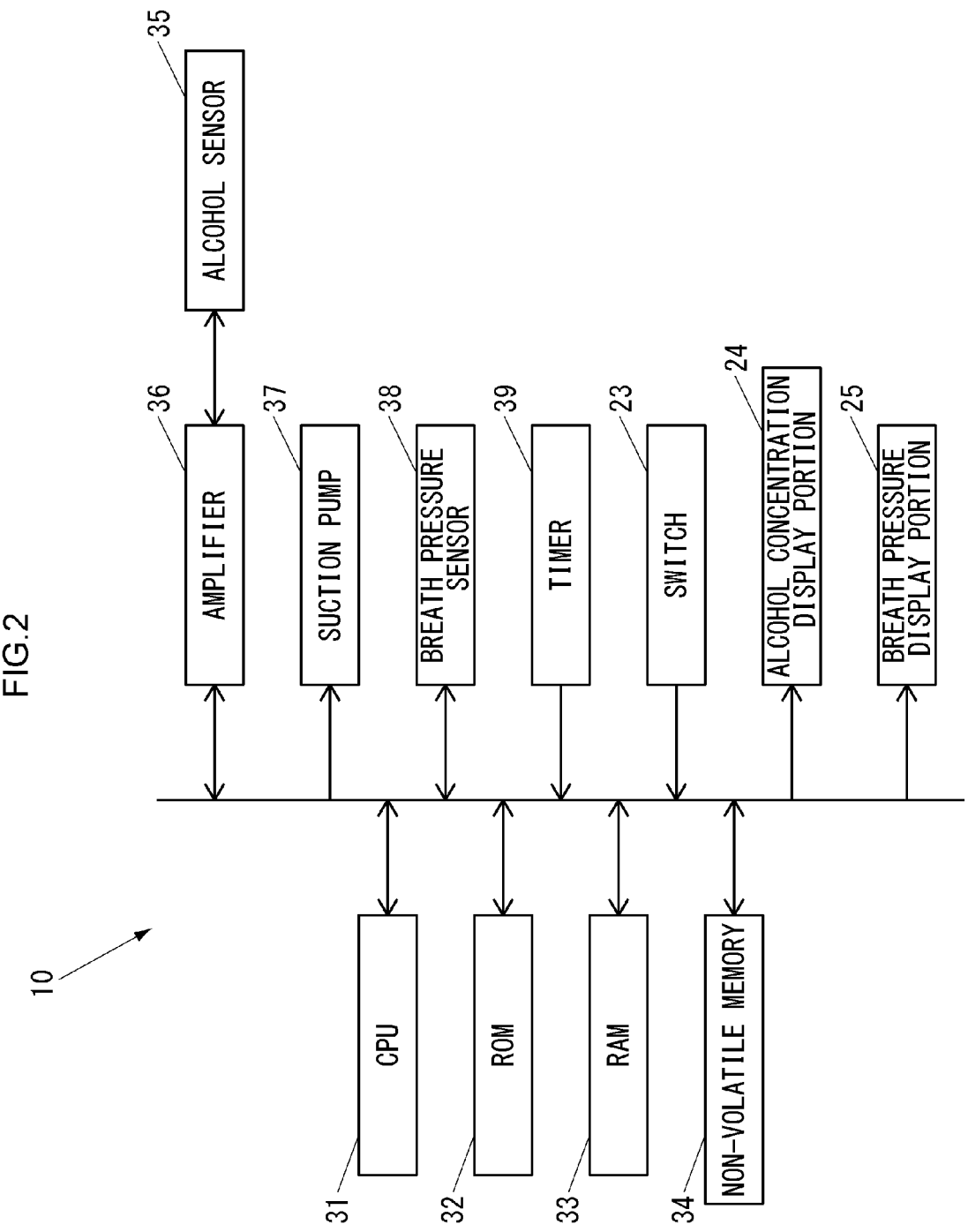
FIG. 2 is a block diagram illustrating the breath alcohol measuring apparatus illustrated in FIG. 1.

FIG. 2 is a block diagram illustrating the breath alcohol measuring apparatus 10.

As illustrated in FIG. 2, the breath alcohol measuring apparatus 10 includes a CPU (Central Processing Unit) 31 for controlling the whole breath alcohol measuring apparatus 10, a ROM (Read Only Memory) 32 that stores beforehand a program or various data pieces for operating the CPU 31, a RAM (Random Access Memory) 33 used for a working area of the CPU 31, a non-volatile memory 34, such as EEPROM (Electrically Erasable Programmable Read Only Memory), for storing a result of a measurement, an alcohol sensor 35 that measures an alcohol concentration in the breath blown into the mouth piece 22, an amplifier 36 that amplifies a signal outputted from the alcohol sensor 35, a suction pump 37 that sucks the breath blown into the mouthpiece 22 for allowing the alcohol sensor 35 to measure the alcohol concentration, a breath pressure sensor 38, serving as the breath force sensor in the present invention, that measures the breath pressure as the force of the breath blown into the mouth piece 22, a timer 39 that counts a time, the above-mentioned switch 23, the alcohol concentration display portion 24, and the breath pressure display portion 25.

The CPU 31, the ROM 32, the RAM 33, the non-volatile memory 34, the alcohol sensor 35, the amplifier 36, the suction pump 37, the breath pressure sensor 38, and the timer 39 are provided in the casing 21.

Figure 3:
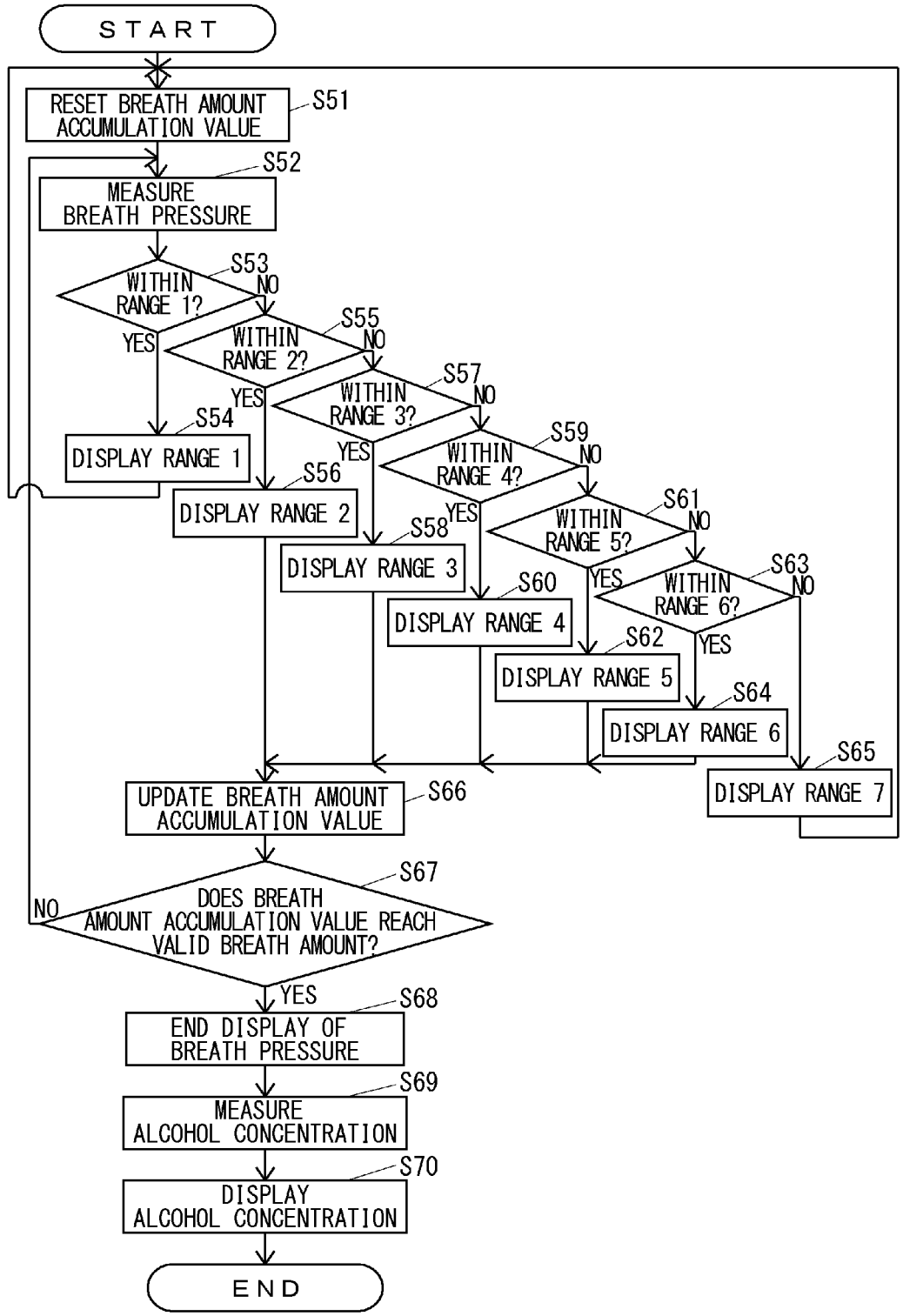
FIG. 3 is a flowchart illustrating the operation of the breath alcohol measuring apparatus illustrated in FIG. 1.

FIG. 3 is a flowchart illustrating the operation of the breath alcohol measuring apparatus 10.

When the to-be-measured person 90 wishes to undergo the measurement of the breath alcohol concentration, he/she depresses the switch 23 of the breath alcohol measuring apparatus 10, and blows into the mouth piece 22. When the to-be-measured person 90 depresses the switch 23, the CPU 31 of the breath alcohol measuring apparatus 10 executes the process illustrated in FIG. 3.

As illustrated in FIG. 3, the CPU 31 resets a breath amount accumulation value stored in the RAM 33 to zero (S51). The breath amount accumulation value is a value by which the CPU 31 determines whether or not the breath amount blown by the to-be-measured person 90 reaches the breath amount that makes the measurement of the alcohol concentration by the alcohol sensor 35 valid (hereinafter referred to as "valid breath amount"). The breath amount accumulation value can be obtained by integrating the flow rate of the breath blown by the to-be-measured person 90 with time. The breath flow rate is proportional to the breath pressure in the breath alcohol measuring apparatus 10, so that it can be obtained from the breath pressure.

Then, the CPU 31 measures the pressure of the breath blown by the to-be-measured person 90 by the breath pressure sensor 38 (S52). The CPU 31 controls the process illustrated in FIG. 3 so as to execute S52 every predetermined time based upon the time counted by the timer 39. The predetermined time is referred to as a breath pressure measurement unit time below.

Next, the CPU 31 determines whether the breath pressure measured in S52 falls within a range 1 or not (S53).

Here, the CPU 31 classifies the breath pressure into 7 levels that are range 1 to range 7. The range 1 is a range of a breath pressure smaller than a minimum breath pressure, which is the minimum value of the breath pressure that makes the measurement of the alcohol concentration by the alcohol sensor 35 valid. The range 7 is a range of the breath pressure larger than a maximum breath pressure, which is the maximum value of the breath pressure that makes the measurement of the alcohol concentration by the alcohol sensor 35 valid. The reason why the minimum breath pressure and the maximum breath pressure are set is because the accurate measurement of the alcohol concentration by the alcohol sensor 35 cannot be made, if there is not a certain amount of breath pressure. The minimum breath pressure and the maximum breath pressure may be the minimum breath pressure and the maximum breath pressure that are provided by the United States Department of Transportation for the breath alcohol measuring apparatus, for example. The range 2 is a range where the breath pressure is the smallest, among five ranges that are formed by dividing the range between the minimum breath pressure and the maximum breath pressure into five. The range 3 is a range where the breath pressure is the second smallest, among the five ranges that are formed by dividing the range between the minimum breath pressure and the maximum breath pressure into five. The range 4 is a range where the breath pressure is the third smallest, among the five ranges that are formed by dividing the range between the minimum breath pressure and the maximum breath pressure into five. The range 5 is a range where the breath pressure is the fourth smallest, among the five ranges that are formed by dividing the range between the minimum breath pressure and the maximum breath pressure into five. The range 6 is a range where the breath pressure is the greatest, among the five ranges that are formed by dividing the range between the minimum breath pressure and the maximum breath pressure into five. The range 2 to the range 6 is the valid range that is the range of the breath pressure by which the measurement of the alcohol concentration by the alcohol sensor 35 is made valid.

Figure 4:
FIG. 4 is a view illustrating a display example of a breath pressure display portion in the breath alcohol measuring apparatus illustrated in FIG. 1.

When the CPU 31 determines in S53 that the breath pressure falls within the range 1, it allows the breath pressure display portion 25 to display the range 1 illustrated in FIG. 4 (S54), and then, returns again to the process in S51. The display of the range 1 is such that the light-emitting members 25a to 25e are all turned off as illustrated in FIG. 4.

When the CPU 31 determines in S53 that the breath pressure does not fall within the range 1, it determines whether the breath pressure measured in S52 falls within the range 2 or not (S55).

When the CPU 31 determines in S55 that the breath pressure falls within the range 2, it allows the breath pressure display portion 25 to display the range 2 illustrated in FIG. 4 (S56). The display of the range 2 is such that only the light-emitting member 25a of the light-emitting members 25a to 25e is lighted as illustrated in FIG. 4.

When the CPU 31 determines in S55 that the breath pressure does not fall within the range 2, it determines whether the breath pressure measured in S52 falls within the range 3 or not (S57).

When the CPU 31 determines in S57 that the breath pressure falls within the range 3, it allows the breath pressure display portion 25 to display the range 3 illustrated in FIG. 4 (S58). The display of the range 3 is such that only the light-emitting members 25a and 25b of the light-emitting members 25a to 25e are lighted as illustrated in FIG. 4.

When the CPU 31 determines in S57 that the breath pressure does not fall within the range 3, it determines whether the breath pressure measured in S52 falls within the range 4 or not (S59).

When the CPU 31 determines in S59 that the breath pressure falls within the range 4, it allows the breath pressure display portion 25 to display the range 4 illustrated in FIG. 4 (S60). The display of the range 4 is such that only the light-emitting members 25*a* to 25*c* of the light-emitting members 25*a* to 25*e* are lighted as illustrated in FIG. 4.

When the CPU 31 determines in S59 that the breath pressure does not fall within the range 4, it determines whether the breath pressure measured in S52 falls within the range 5 or not (S61).

When the CPU 31 determines in S61 that the breath pressure falls within the range 5, it allows the breath pressure display portion 25 to display the range 5 illustrated in FIG. 4 (S62). The display of the range 5 is such that only the light-emitting members 25*a* to 25*d* of the light-emitting members 25*a* to 25*e* are lighted as illustrated in FIG. 4.

When the CPU 31 determines in S61 that the breath pressure does not fall within the range 5, it determines whether the breath pressure measured in S52 falls within the range 6 or not (S63).

When the CPU 31 determines in S63 that the breath pressure falls within the range 6, it allows the breath pressure display portion 25 to display the range 6 illustrated in FIG. 4 (S64). The display of the range 6 is such that all of the light-emitting members 25*a* to 25*e* are lighted as illustrated in FIG. 4.

When the CPU 31 determines in S63 that the breath pressure does not fall within the range 6, it allows the breath pressure display portion 25 to display the range 7 illustrated in FIG. 4 (S65), and then, returns again to the process in S51. The display of the range 7 is such that all of the light-emitting members 25*a* to 25*e* are lighted as illustrated in FIG. 4.

When the CPU 31 ends the process in S56, S58, S60, S62 or S64, it adds the product of the flow rate of the breath corresponding to the breath pressure measured in S52 and the breath pressure measurement unit time to the breath amount accumulation value stored in the RAM 33, thereby updating the breath amount accumulation value stored in the RAM 33 (S66).

Then, the CPU 31 determines whether the breath amount accumulation value stored in the RAM 33 reaches the valid breath amount or not (S67). The reason why the valid breath amount is set in S67 is as described below. Specifically, if the alcohol concentration is measured when the air volume blown into the mouth piece 22 by the to-be-measured person 90 is small, the alcohol concentration of fresh air that has just entered the mouth of the to-be-measured person 90 might be measured. Therefore, it is necessary that a certain volume of air is blown in order to measure the alcohol concentration of the breath, i.e., of the air in the lung. The valid breath amount is set to be 1 L, for example.

When the CPU 31 determines in S67 that the breath amount accumulation value does not reach the valid breath amount, it executes again the process in S52.

On the other hand, when the CPU 31 determines in S67 that the breath amount accumulation value reaches the valid breath amount, it allows the breath pressure display portion 25 to end the display of the breath pressure (S68), and then, drives the suction pump 37 so as to execute the measurement of the alcohol concentration by the alcohol sensor 35 (S69).

Next, the CPU 31 allows the alcohol concentration display portion 24 to display the alcohol concentration measured in S69 (S70), and then, ends the process illustrated in FIG. 3. It is to be noted that the CPU 31 deletes the alcohol concentration displayed in S70 with a lapse of a predetermined time.

Figure 5:
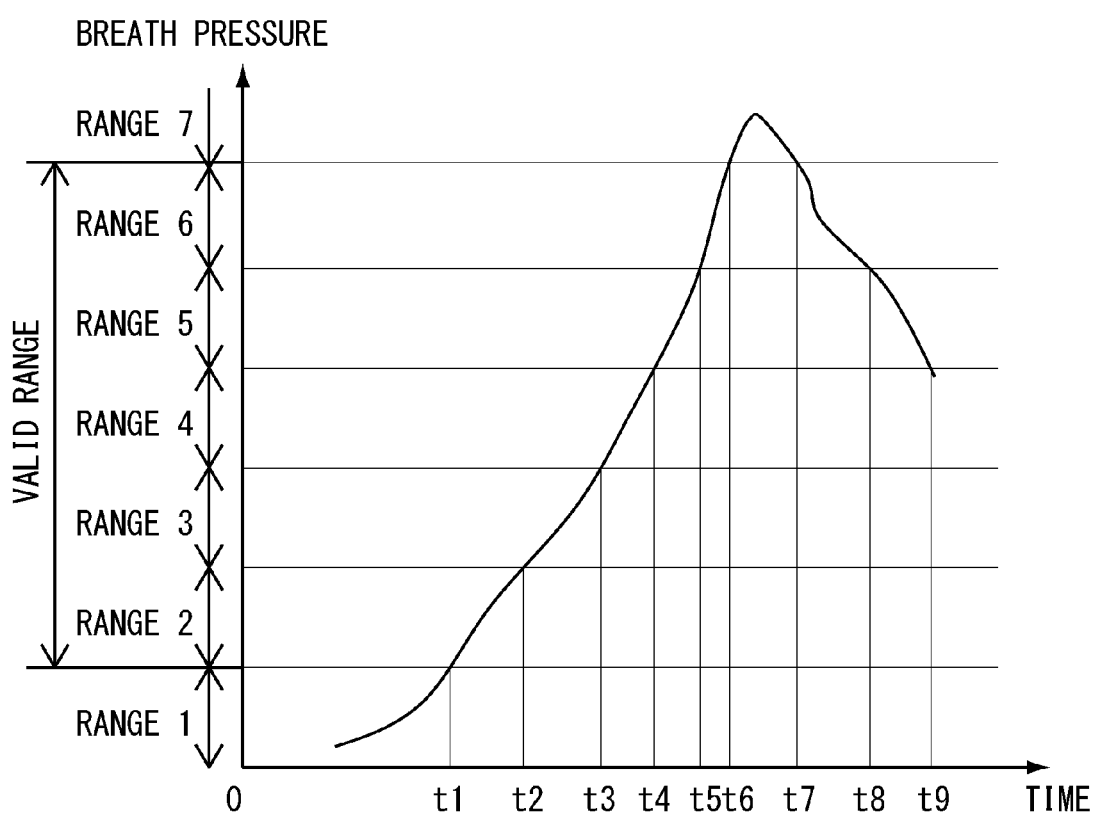
FIG. 5 is a view illustrating an example of the breath pressure blown into a mouth piece illustrated in FIG. 1 by a to-be-measured person.

FIG. 5 is a view illustrating an example of the pressure of the breath blown into the mouth piece 22 by the to-be-measured person 90.

When the to-be-measured person 90 depresses the switch 23, the CPU 31 executes the process illustrated in FIG. 3 as described above. Therefore, when the to-be-measured person 90 blows into the mouth piece 22 as illustrated in FIG. 5, the breath pressure display portion 25 displays the range 1 illustrated in FIG. 4 during the period from a time 0 to a time t1, displays the range 2 illustrated in FIG. 4 during the period from the time t1 to a time t2, displays the range 3 illustrated in FIG. 4 during the period from the time t2 to a time t3, displays the range 4 illustrated in FIG. 4 during the period from the time t3 to a time t4, displays the range 5 illustrated in FIG. 4 during the period from the time t4 to a time t5, displays the range 6 illustrated in FIG. 4 during the period from the time t5 to a time t6, displays the range 7 illustrated in FIG. 4 during the period from the time t6 to a time t7, displays the range 6 illustrated in FIG. 4 during the period from the time t7 to a time t8, and displays the range 5 illustrated in FIG. 4 during the period from the time t8 to a time t9.

As described above, in the breath alcohol measuring apparatus 10, the breath pressure display portion 25 is arranged at the position that can be visually recognized by the to-be-measured person 90 who is blowing into the mouth piece 22. Therefore, the breath alcohol measuring apparatus 10 can allow the to-be-measured person 90, who is blowing, to recognize the breath pressure.

In the breath alcohol measuring apparatus 10, the breath pressure display portion 25 displays the breath pressure within the valid range including plural levels such as from the range 2 to the range 6. Therefore, the to-be-measured person 90 can recognize at which level within the valid range the current breath pressure is placed. Accordingly, the breath alcohol measuring apparatus 10 can allow the to-be-measured person 90 to easily keep the breath pressure within the valid range, compared to the configuration that displays as to only whether the breath pressure falls within the valid range or not, i.e., the configuration that displays the valid range with only one level.

In the breath alcohol measuring apparatus 10, the breath pressure display portion 25 includes plural light-emitting members 25*a* to 25*e* that display the breath pressure with plural levels. Therefore, it can allow the to-be-measured person 90 to easily recognize whether the breath pressure is appropriate or not, compared to the configuration in which the breath pressure display portion 25 displays the breath pressure with a numerical value.

In the breath alcohol measuring apparatus 10, the plural light-emitting members 25*a* to 25*e* are arranged side by side in the order of the corresponding level of the breath pressure as illustrated in FIG. 4. Therefore, it can allow the to-be-measured person 90 to easily recognize whether the breath pressure is appropriate or not, compared to the configuration in which the plural light-emitting members 25*a* to 25*e* are arranged regardless of the order of the level of the breath pressure.

In the breath alcohol measuring apparatus 10, the light-emitting member 25*c*, which corresponds to the range 4 that is the middle level of the valid range, emits light in a different form from those of the other light-emitting members 25*a*, 25*b*, 25*d*, and 25*e*. Therefore, the breath alcohol measuring apparatus 10 can allow the to-be-measured person 90 to easily recognize the range 4 that is the middle level of the valid range. Accordingly, the breath alcohol measuring apparatus 10 allows the to-be-measured person 90 to adjust the breath pressure such that the range 4 is displayed, thereby being capable of allowing the to-be-measured person 90 to easily keep the breath force within the valid range.

In the breath alcohol measuring apparatus 10, the light-emitting member 25c emits light with an emission color different from the emission lights from the other light-emitting members 25a, 25b, 25d, and 25e. However, it may emit light in a different form other than the emission color. For example, the light-emitting member 25c may emit light in a different form from the other light-emitting members 25a, 25b, 25d, and 25e, by the size of an illuminant, the brightness of the emission, or flickering speed.

The breath alcohol measuring apparatus 10 may be configured such that the light-emitting member 25c corresponding to the range 4 that is the middle level of the valid range emits light in the same form as in the other light-emitting members 25a, 25b, 25d, and 25e.

In the breath alcohol measuring apparatus 10, the breath pressure display portion 25 makes the same display for the level 6, which is the level adjacent to a level outside the valid range, among the plural levels within the valid range, and for the level 7 which is the level outside the valid range and which is adjacent to the level 6. Specifically, the breath pressure display portion 25 displays the levels 6 and 7 with all of the light-emitting members 25a to 25e being lighted. Therefore, even when the breath pressure changes, when it is within the valid range, to become the level 6, which is indicated by the display being the same as the display for the level 7 that is the level outside the valid range, the breath pressure is still on the level 6 within the valid range immediately after the breath pressure display portion 25 makes this display. Accordingly, the breath alcohol measuring apparatus 10 allows the to-be-measured person 90 to adjust such that this display is not made, thereby being capable of allowing the to-be-measured person 90 to easily keep the breath pressure within the valid range. In the breath alcohol measuring apparatus 10, the range 6 that is the level within the valid range is indicated by the display being the same as the display for the range 7 that is the level outside the valid range. Therefore, the number of the light-emitting members can be reduced, compared to the configuration in which the level 6 is indicated by the display different from the display for the level 7.

The to-be-measured person 90 adjusts the breath pressure as confirming the display on the breath pressure display portion 25 such that the breath pressure display portion 25 displays the range 4. If the breath pressure is outside the range 4, the to-be-measured person 90 adjusts again the breath pressure as confirming the display on the breath pressure display portion 25 in order to get the breath pressure back to the range 4. In this case, the to-be-measured person 90 takes care not to cause the breath pressure to be smaller than the lower limit of the range 3, or not to cause the breath pressure to be larger than the upper limit of the range 5. Accordingly, the to-be-measured person 90 can easily keep the breath pressure within the valid range.

In the breath alcohol measuring apparatus 10, the ranges 1 to 7 are displayed according to the number of the light-emitting members 25a to 25e to be lighted as illustrated in FIG. 4. However, only one of the light-emitting members 25a to 25e corresponding respectively to the ranges 1 to 7 may be lighted as illustrated in FIG. 6.

In the breath alcohol measuring apparatus 10, as the breath pressure increases from the range 1 toward the range 7, the light-emitting members are lighted from the light-emitting member 25a, which is the leftmost light-emitting member, toward the light-emitting member 25e, which is the rightmost light-emitting member, as viewed from the to-be-measured person 90 who is blowing into the mouth piece 22. However, the light-emitting members may be lighted from the light-emitting member 25e that is the rightmost light-emitting member to the light-emitting member 25a that is the leftmost light-emitting member.

In the breath alcohol measuring apparatus 10, the light-emitting members 25a to 25e are arranged laterally as viewed from the to-be-measured person 90 who is blowing into the mouth piece 22. However, the light-emitting members 25a to 25e may be arranged in the form other than the lateral arrangement. For example, as illustrated in FIG. 7A, in the breath alcohol measuring apparatus 10, the light-emitting members 25a to 25e may be arranged longitudinally as viewed from the to-be-measured person 90 who is blowing into the mouth piece 22, or as illustrated in FIG. 7B, the light-emitting members 25a to 25e may be arranged in a Y-shaped form as viewed from the to-be-measured person 90 who is blowing into the mouth piece 22.

Figure 7A:
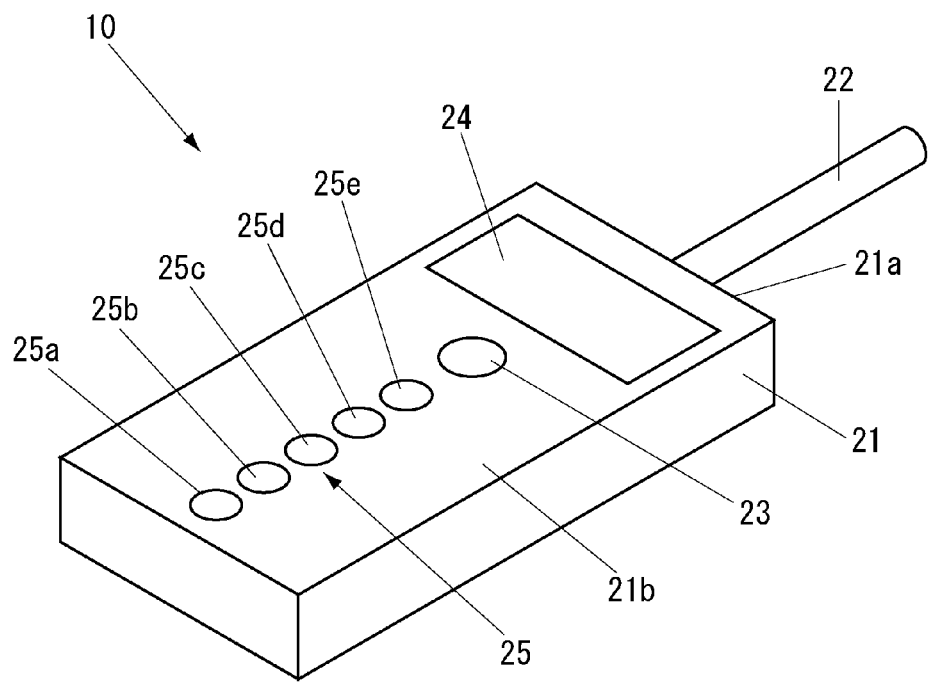
FIG. 7A is a view illustrating an example, different from the example illustrated in FIG. 1, of the breath alcohol measuring apparatus illustrated in FIG. 1.

Even when the light-emitting members 25a to 25e are arranged as illustrated in FIG. 7A, the breath alcohol measuring apparatus 10 can provide the operation and effect being the same as the operation and effect in the case in which they are arranged as illustrated in FIG. 1. For example, as illustrated in FIG. 4 or 6, in the breath alcohol measuring apparatus 10, as the breath pressure increases from the range 1 to the range 7, the light-emitting members may be lighted from the light-emitting member 25a that is the uttermost light-emitting member to the light-emitting member 25e that is the nearest light-emitting member, as viewed from the to-be-measured person 90 who is blowing into the mouth piece 22. Alternatively, the light emitting members may be lighted from the light-emitting member 25e that is the nearest light-emitting member to the light-emitting member 25a that is the uttermost light-emitting member.

Figure 7B:
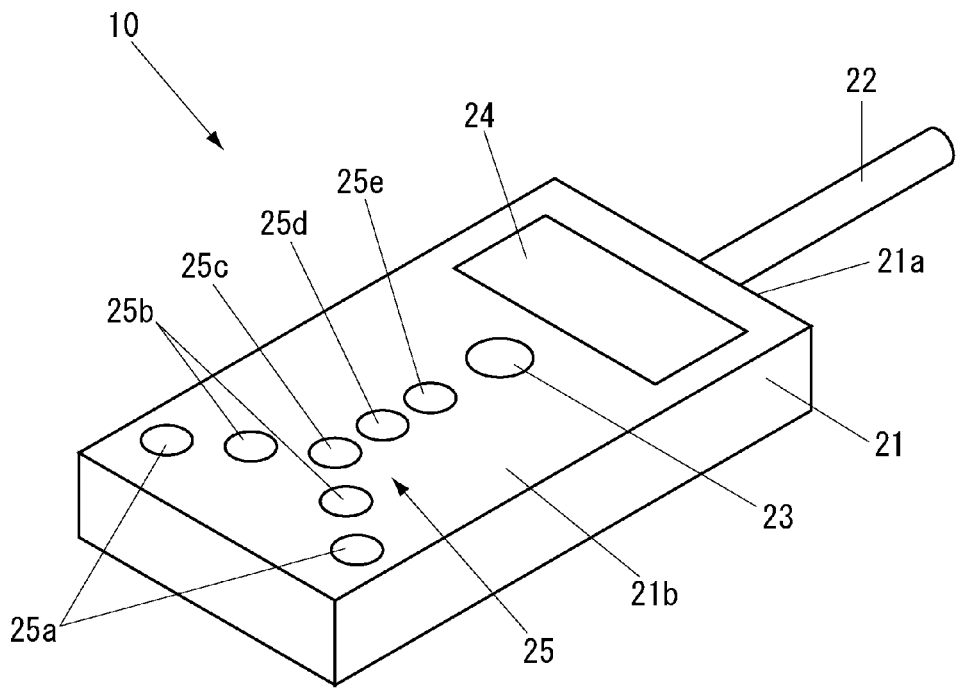
FIG. 7B is a view illustrating an example, different from the examples illustrated in FIGS. 1 and 7A, of the breath alcohol measuring apparatus illustrated in FIG. 1.

Similarly, even when the light-emitting members 25a to 25e are arranged as illustrated in FIG. 7B, the breath alcohol measuring apparatus 10 can provide the operation and effect being the same as the operation and effect in the case in which they are arranged as illustrated in FIG. 1. In FIG. 7B, two light-emitting members 25a are arranged, and they make the same operation. Similarly, in FIG. 7B, two light-emitting members 25b are arranged, and they make the same operation.

In the breath alcohol measuring apparatus 10, the breath pressure display portion 25 may have a light-emitting member corresponding to the range 7, whereby the range 6 may be indicated by the display different from the display for the range 7.

In the breath alcohol measuring apparatus 10, the plural light-emitting members 25a to 25e may be arranged regardless of the order of the level of the breath pressure.

Figure 8A:
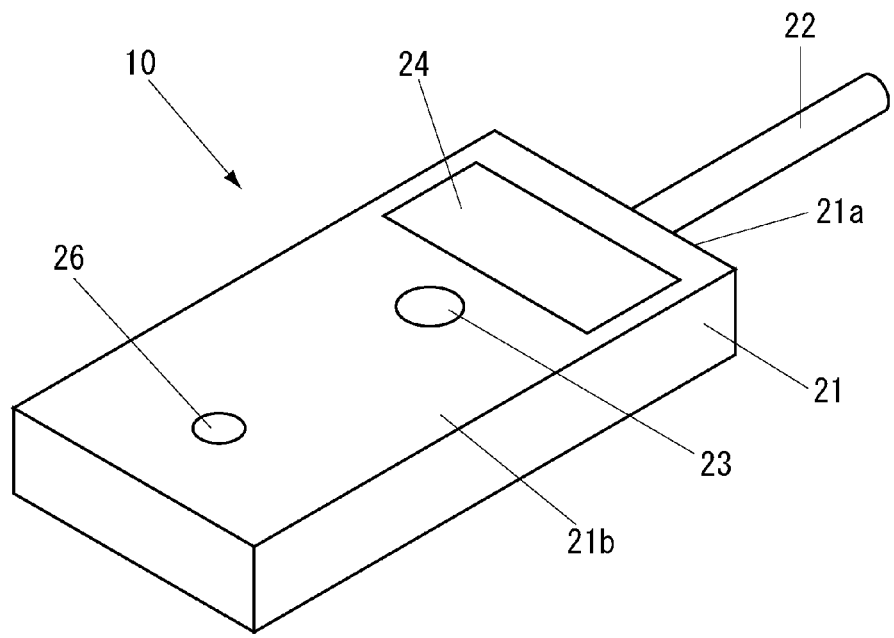
FIG. 8A is a view illustrating an example, different from the examples illustrated in FIGS. 1 and 7, of the breath alcohol measuring apparatus illustrated in FIG. 1.
Figure 8B:
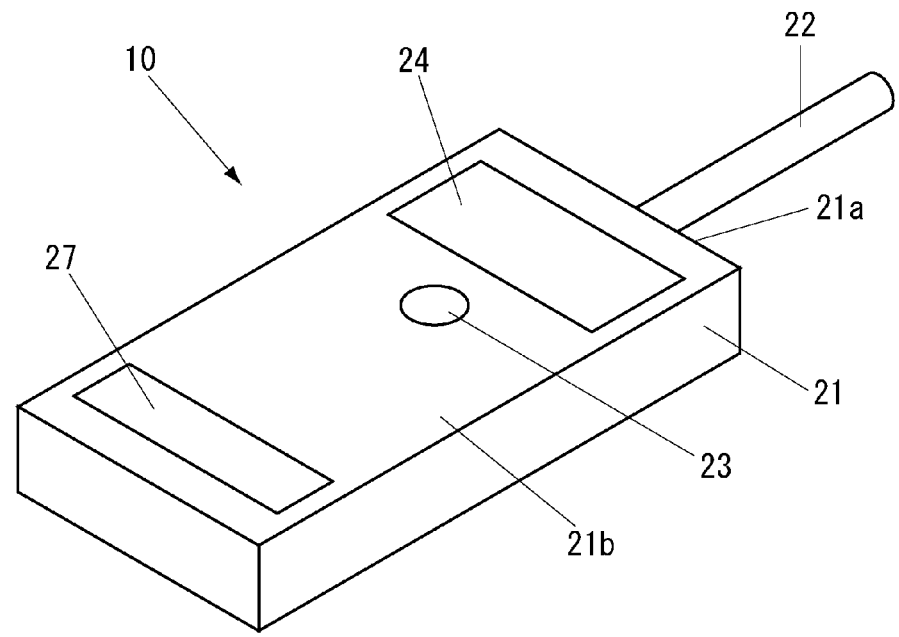
FIG. 8B is a view illustrating an example, different from the examples illustrated in FIGS. 1, 7, and 8A, of the breath alcohol measuring apparatus illustrated in FIG. 1.

In the breath alcohol measuring apparatus 10, the breath force display portion includes the plural light-emitting members 25a to 25e. However, the breath force display portion may have a configuration other than the plural light-emitting members 25a to 25e. For example, in the breath alcohol measuring apparatus 10, the breath force display portion may include one light-emitting member 26, which indicates the plural levels of the breath pressure by changing the color of the emitted light as illustrated in FIG. 8A. Alternatively, as illustrated in FIG. 8B, the breath force display portion may be a display device 27 such as an LCD that displays the breath pressure with an optional indication such as a numerical value.

When the breath force display portion in the breath alcohol measuring apparatus 10 includes one light-emitting member 26, which indicates the plural levels of the breath pressure by changing the color of the emitted light as illustrated in FIG. 8A, the arrangement space of the light-emitting member can be reduced, compared to the configuration in which breath pressure is indicated by the plural light-emitting members 25a to 25e. The light-emitting member 26 may indicate the breath pressure with plural levels by changing the emission form, other than the color of the emitted light. For example, the light-emitting member 26 may indicate the breath pressure with the plural levels by changing the brightness of the emitted light or flickering speed.

The breath alcohol measuring apparatus 10 indicates the valid range with 5 levels. However, the breath alcohol measuring apparatus 10 may indicate the valid range with plural levels other than 5 levels. The breath alcohol measuring apparatus 10 may indicate the valid range with only 1 level.

Second Embodiment

A configuration of a breath alcohol measuring apparatus according to the second embodiment of the present invention will be described. The components being the same as the components of the breath alcohol measuring apparatus 10 (see FIG. 1) according to the first embodiment, among the components of the breath alcohol measuring apparatus according to the present embodiment, are identified by the same numerals, and the detailed description thereof will not be repeated here.

Figure 9:
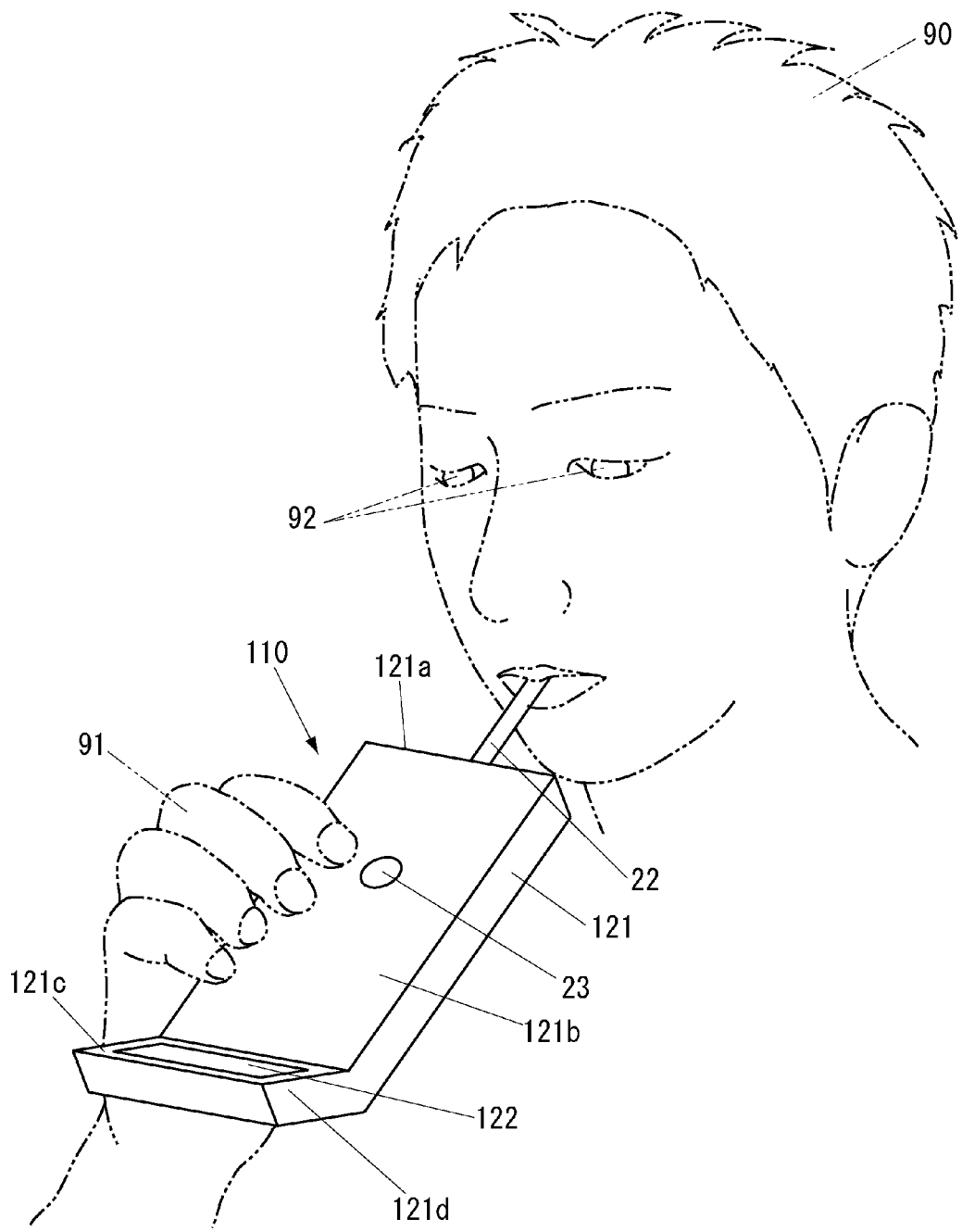
FIG. 9 is a perspective view illustrating an appearance of a breath alcohol measuring apparatus according to a second embodiment of the present invention.

FIG. 9 is a perspective view illustrating an appearance of a breath alcohol measuring apparatus 110 according to the present embodiment.

As illustrated in FIG. 9, the breath alcohol measuring apparatus 110 has a casing 121 instead of the casing 21 (see FIG. 1) of the breath alcohol measuring apparatus 10, and a display portion 122 serving as the breath force display portion in the present invention instead of the alcohol concentration display portion 24 and the breath pressure display portion 25 (see FIG. 1) of the breath alcohol measuring apparatus 10.

The casing 121 is held by the hand 91 of the to-be-measured person 90, and is provided with the mouth piece 22 and the switch 23. Like the breath alcohol measuring apparatus 10, the CPU 31, the ROM 32, the RAM 33, the non-volatile memory 34, the alcohol sensor 35, the amplifier 36, the suction pump 37, the breath pressure sensor 38, and the timer 39 (see FIG. 2) are provided in the casing 121.

The casing 121 has a surface 121a on which an unillustrated breath injecting port to which the mouth piece 22 is inserted is formed, a surface 121b that is adjacent to the surface 121a and on which the switch 23 is provided, and a surface 121c that is adjacent to the surface 121b and on which the display portion 122 is provided.

The display portion 122 is a display device such as an LCD for displaying the alcohol concentration in the breath blown into the mouth piece 22, and the breath pressure that is the pressure of the breath blown into the mouth piece 22. The display portion 122 is arranged at the position on a portion 121d that projects from the surface 121b of the casing 121, and at the position opposite to eyes 92 of the to-be-measured person 90 who is blowing into the mouth piece 22.

As described above, in the breath alcohol measuring apparatus 110, the display portion is arranged at the position on the portion 121d that projects from the surface 121b of the casing 121, and at the position opposite to the eyes 92 of the to-be-measured person 90 who is blowing into the mouth piece 22. Therefore, the breath alcohol measuring apparatus 110 can allow the to-be-measured person 90, who is blowing, to easily recognize visually the display portion 122.

In the breath alcohol measuring apparatus 110, the breath pressure display portion according to the present invention may have a configuration other than the LCD. For example, the breath alcohol measuring apparatus 110 may have the configuration being the same as the configuration of plural light-emitting members 25a to 25e (see FIG. 1) or a single light-emitting member 26 (see FIG. 8A) according to the first embodiment on the surface 121c as the breath pressure display portion according to the present invention.

The portion 121d is formed to project from the surface 121b not only by bending apart of the casing 121 as illustrated in FIG. 9 but also by forming a convex portion on a part of the casing 121.

In the above-mentioned embodiments, the breath pressure is used as the breath force. However, the flow rate of the breath may be used as the breath force. A flow rate sensor may be used as the breath force sensor in the present invention.

In the above-mentioned embodiments, the mouth piece 22 that is provided detachably to the casing 21 is mounted as the breath blowing portion in the present invention. However, a breath blowing portion that is mounted to the casing 21 so as not to be detachable, that is held by the to-be-measured person 90 with his/her mouth, and into which the breath is blown, may be provided. Alternatively, a breath blowing portion into which the breath is blown by blowing the breath by the to-be-measured person 90 without being held by the to-be-measured person 90 with his/her mouth may be provided.

What is claimed is:

1. A breath alcohol measuring apparatus comprising: a casing that is held by a hand of a to-be-measured person during a measurement; a breath blowing portion that is provided to the casing, and into which a breath of the to-be-measured person is blown; an alcohol sensor that measures an alcohol concentration of the breath blown into the breath blowing portion; a breath force sensor that measures a force of the breath blown into the breath blowing portion; a breath force display portion that is provided to the casing for displaying the force measured by the breath force sensor; and a CPU, wherein, when the force is kept to fall within a valid range, which is the range of the force that makes the measurement of the alcohol concentration by the alcohol sensor valid, the CPU updates a breath amount accumulation value that is an accumulation value of the amount of the breath blown into the breath blowing portion; when the force is placed outside the valid range, the CPU resets the breath amount accumulation value; and when the breath amount accumulation value reaches a valid breath amount, which is the breath amount that makes the measurement of the alcohol concentration by the alcohol sensor valid, the CPU measures the alcohol concentration by the alcohol sensor, and the breath force display portion is arranged at the position that can be visually recognized by the to-be-measured person who is blowing into the breath blowing portion.

2. A breath alcohol measuring apparatus according to claim 1, wherein the breath force display portion indicates the valid range, which is the range of the force that makes the measurement of the alcohol concentration by the alcohol sensor valid, with plural levels.

3. A breath alcohol measuring apparatus according to claim 2, wherein the breath force display portion includes plural light-emitting members that display the force with plural levels.

4. A breath alcohol measuring apparatus according to claim 3, wherein the plural light-emitting members are arranged side by side in an order of a corresponding level of the force.

5. A breath alcohol measuring apparatus according to claim 3, wherein the light-emitting member corresponding to the middle level in the valid range emits light in a form different from those of the other light-emitting members.

6. A breath alcohol measuring apparatus according to claim 5, wherein the breath force display portion indicates at least one level, which is adjacent to a level outside the valid range, of the plural levels within the valid range, and the level outside the valid range adjacent to this level, with the same display.

7. A breath alcohol measuring apparatus according to claim 6, wherein the breath force display portion is arranged at the position on a projecting portion of the casing, and at the position opposite to eyes of the to-be-measured person who is blowing into the breath blowing portion.

8. A breath alcohol measuring apparatus according to claim 5, wherein the breath force display portion is arranged at the position on a projecting portion of the casing, and at the position opposite to eyes of the to-be-measured person who is blowing into the breath blowing portion.

9. A breath alcohol measuring apparatus according to claim 4, wherein the breath force display portion indicates at least one level, which is adjacent to a level outside the valid range, of the plural levels within the valid range, and the level outside the valid range adjacent to this level, with the same display.

10. A breath alcohol measuring apparatus according to claim 9, wherein the breath force display portion is arranged at the position on a projecting portion of the casing, and at the position opposite to eyes of the to-be-measured person who is blowing into the breath blowing portion.

11. A breath alcohol measuring apparatus according to claim 4, wherein the breath force display portion is arranged at the position on a projecting portion of the casing, and at the position opposite to eyes of the to-be-measured person who is blowing into the breath blowing portion.

12. A breath alcohol measuring apparatus according to claim 3, wherein the breath force display portion indicates at least one level, which is adjacent to a level outside the valid range, of the plural levels within the valid range, and the level outside the valid range adjacent to this level, with the same display.

13. A breath alcohol measuring apparatus according to claim 12, wherein the breath force display portion is arranged at the position on a projecting portion of the casing, and at the position opposite to eyes of the to-be-measured person who is blowing into the breath blowing portion.

14. A breath alcohol measuring apparatus according to claim 3, wherein the light-emitting member corresponding to the middle level in the valid range emits light in a form different from those of the other light-emitting members.

15. A breath alcohol measuring apparatus according to claim 14, wherein the breath force display portion indicates at least one level, which is adjacent to a level outside the valid range, of the plural levels within the valid range, and the level outside the valid range adjacent to this level, with the same display.

16. A breath alcohol measuring apparatus according to claim 15, wherein the breath force display portion is arranged at the position on a projecting portion of the casing, and at the position opposite to eyes of the to-be-measured person who is blowing into the breath blowing portion.

17. A breath alcohol measuring apparatus according to claim 14, wherein the breath force display portion is arranged at the position on a projecting portion of the casing, and at the position opposite to eyes of the to-be-measured person who is blowing into the breath blowing portion.

18. A breath alcohol measuring apparatus according to claim 3, wherein the breath force display portion is arranged at the position on a projecting portion of the casing, and at the position opposite to eyes of the to-be-measured person who is blowing into the breath blowing portion.

19. A breath alcohol measuring apparatus according to claim 2, wherein the breath force display portion includes a single light-emitting member that indicates the force with the plural levels by changing a light-emitting form.

20. A breath alcohol measuring apparatus according to claim 19, wherein the breath force display portion is arranged at the position on a projecting portion of the casing, and at the position opposite to eyes of the to-be-measured person who is blowing into the breath blowing portion.

21. A breath alcohol measuring apparatus according to claim 2, wherein the breath force display portion is arranged at the position on a projecting portion of the casing, and at the position opposite to eyes of the to-be-measured person who is blowing into the breath blowing portion.

22. A breath alcohol measuring apparatus according to claim 1, wherein the breath force display portion is arranged at the position on a projecting portion of the casing, and at the position opposite to eyes of the to-be-measured person who is blowing into the breath blowing portion.

* * * * *